US008144317B1

(12) United States Patent
Joyce

(10) Patent No.: US 8,144,317 B1
(45) Date of Patent: Mar. 27, 2012

(54) METHOD TO LOCATE AND ELIMINATE MANUFACTURING DEFECTS IN A QUARTZ RESONATOR GYRO

(75) Inventor: Richard J. Joyce, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 13/075,784

(22) Filed: Mar. 30, 2011

Related U.S. Application Data

(62) Division of application No. 12/269,590, filed on Nov. 12, 2008, now Pat. No. 7,972,552.

(51) Int. Cl.
*G01N 21/00* (2006.01)
(52) U.S. Cl. .......... 356/237.4; 264/400; 356/237.1; 382/145; 382/149
(58) Field of Classification Search .... 356/237.1–237.6; 264/400; 382/149, 147, 145
See application file for complete search history.

(56) References Cited

U.S. PATENT DOCUMENTS

| 6,175,645 B1 * | 1/2001 | Elyasaf et al. ............ 382/147 |
| 6,747,243 B1 * | 6/2004 | Reinhardt ............ 219/121.69 |
| 2004/0156539 A1 * | 8/2004 | Jansson et al. ............ 382/145 |
| 2006/0072807 A1 * | 4/2006 | Bultman et al. ............ 382/149 |
| 2007/0017287 A1 | 1/2007 | Kubena et al. ............ 73/504.02 |
| 2008/0088384 A1 * | 4/2008 | Ichikawa ............ 331/158 |

* cited by examiner

*Primary Examiner* — Gregory J Toatley
*Assistant Examiner* — Iyabo S Alli
(74) *Attorney, Agent, or Firm* — Ladas & Parry

(57) ABSTRACT

A method for locating and eliminating defects on a substrate wafer includes illuminating a top surface of the substrate wafer with a first illumination source, illuminating a bottom surface of the substrate wafer with a second illumination source, forming an image of a portion of the top surface of the substrate wafer while the substrate wafer is illuminated by the first and second illumination sources, adjusting a contrast of the image to accentuate defects on the top surface of the substrate wafer, locating defects in the image, and ablating the defects on the top surface with a laser.

9 Claims, 5 Drawing Sheets

METHOD TO LOCATE AND ELIMINATE MANUFACTURING DEFECTS IN A QUARTZ RESONATOR GYRO

This is a divisional application of U.S. patent application Ser. No. 12/269,590, filed on Nov. 12, 2008, which is incorporated herein as though set forth in full.

GOVERNMENT SPONSORED RESEARCH OR DEVELOPMENT

This invention was made with Government support under Contract No. FA8650-05-C-7245 awarded by DARPA. The Government has certain rights in the invention

BACKGROUND

The present disclosure relates to a method and apparatus for locating and eliminating manufacturing defects for microelectromechanical systems MEMS devices, such as quartz disc resonator used in disk resonator gyroscopes (DRGs). In particular, it relates to using an optical system to locate defects and a laser ablative system to remove defects relating to unwanted excess material on the device. A description of a DRG design can be found in U.S. patent application Ser. No. 11/458,911 filed Jul. 20, 2006 and entitled "Disc Resonator Gyroscopes," which is hereby incorporated by reference as though set forth in full.

SUMMARY OF THE INVENTION

In a first embodiment disclosed herein, a method for locating and eliminating defects on a substrate wafer includes illuminating a top surface of the substrate wafer with a first illumination source, illuminating a bottom surface of the substrate wafer with a second illumination source, forming an image of a portion of the top surface of the substrate wafer while the substrate wafer is illuminated by the first and second illumination sources, adjusting a contrast of the image to accentuate defects on the top surface of the substrate wafer, locating defects in the image, and ablating the defects on the top surface with a laser.

In an aspect of this embodiment the bottom surface of the substrate wafer is affixed to an adjustable transparent base.

In another aspect of this embodiment the step of adjusting a contrast of the image to accentuate defects comprises adjusting the first illumination source, the second illumination source, or the image.

In yet another aspect of this embodiment the laser comprises an excimer laser.

In another aspect of this embodiment the method further comprises repeating the imaging, adjusting, locating, and ablating steps over the entire substrate wafer.

In yet another aspect of this embodiment the substrate wafer comprises quartz, the first illumination source comprises visible light, and the second illumination source comprises visible light.

In still another aspect of this embodiment the laser comprises a 193 nm wavelength ultraviolet excimer laser capable of ablating quartz.

In another aspect of this embodiment the substrate wafer comprises silicon, the first illumination source comprises infrared illumination, and the second illumination source comprises infrared illumination.

In yet another aspect of this embodiment the substrate wafer is at least partially reflective of the first illumination source and the substrate wafer is at least partially opaque to the second illumination source.

In another aspect of this embodiment the substrate wafer comprises a quartz disc resonator for use in a disk resonator gyroscope (DRGs).

In yet another aspect of this embodiment locating defects in the image of the substrate wafer further comprises aiming the laser at the defect.

In another embodiment disclosed herein, an apparatus for locating and eliminating defects on a substrate wafer includes an adjustable transparent base for holding a bottom surface of the substrate wafer. a first illumination source for illuminating a top surface of the substrate wafer, a second illumination source for illuminating the bottom surface of the substrate wafer, an imaging system aligned to form an image of a portion of the top surface of the substrate wafer, the imaging system adapted to find defects in the image, and a laser aligned to the top surface of the substrate wafer for ablating the defects.

In another aspect of this embodiment the imaging system comprises at least one adjustment for adjusting a contrast of the image.

In another aspect of this embodiment the substrate wafer comprises quartz, the first illumination source comprises visible light, and the second illumination source comprises visible light.

In yet another aspect of this embodiment the laser comprises a 193 nm wavelength ultraviolet excimer laser capable of ablating quartz.

In another aspect of this embodiment the substrate wafer comprises silicon, the first illumination source comprises infrared illumination, and the second illumination source comprises infrared illumination.

In another aspect of this embodiment the substrate wafer is at least partially reflective of the first illumination source, and the substrate wafer is at least partially opaque to the second illumination source.

In yet another aspect of this embodiment the substrate wafer comprises a quartz disc resonator for a disk resonator gyroscope (DRGs).

In another aspect of this embodiment the apparatus further comprises a first lens between the first illumination source and the substrate wafer, the first lens adjustable to adjust a contrast of the image, and a second lens between the second illumination source and the substrate wafer, the second lens adjustable to adjust the contrast of the image.

In yet another aspect of this embodiment the apparatus further comprises a first partially reflective mirror between the first illumination source and the substrate wafer for coupling an output of the laser to the substrate wafer, and a second partially reflective mirror in the first path for coupling the imaging system for imaging of the top surface of the substrate wafer.

In yet another embodiment disclosed herein, a method for locating and eliminating defects on a quartz disc resonator for use in a disk resonator gyroscope (DRGs) comprises illuminating a top surface of the quartz disc resonator with a first illumination source, illuminating a bottom surface of the quartz disc resonator with a second illumination source, forming an image of a portion of the top surface of the quartz disc resonator while the quartz disc resonator is illuminated by the first and second illumination sources, adjusting a contrast of the image to accentuate defects on the top surface of the quartz disc resonator, locating defects in the image, and ablating the defects on the top surface with a laser.

In an aspect of this embodiment adjusting a contrast of the image to accentuate defects further comprises adjusting the first illumination source, the second illumination source, or the image.

In another aspect of this embodiment the laser comprises a ultraviolet excimer laser.

These and other features and advantages will become further apparent from the detailed description and accompanying figures that follow. In the figures and description, numerals indicate the various features, like numerals referring to like features throughout both the drawings and the description.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Figure 1:
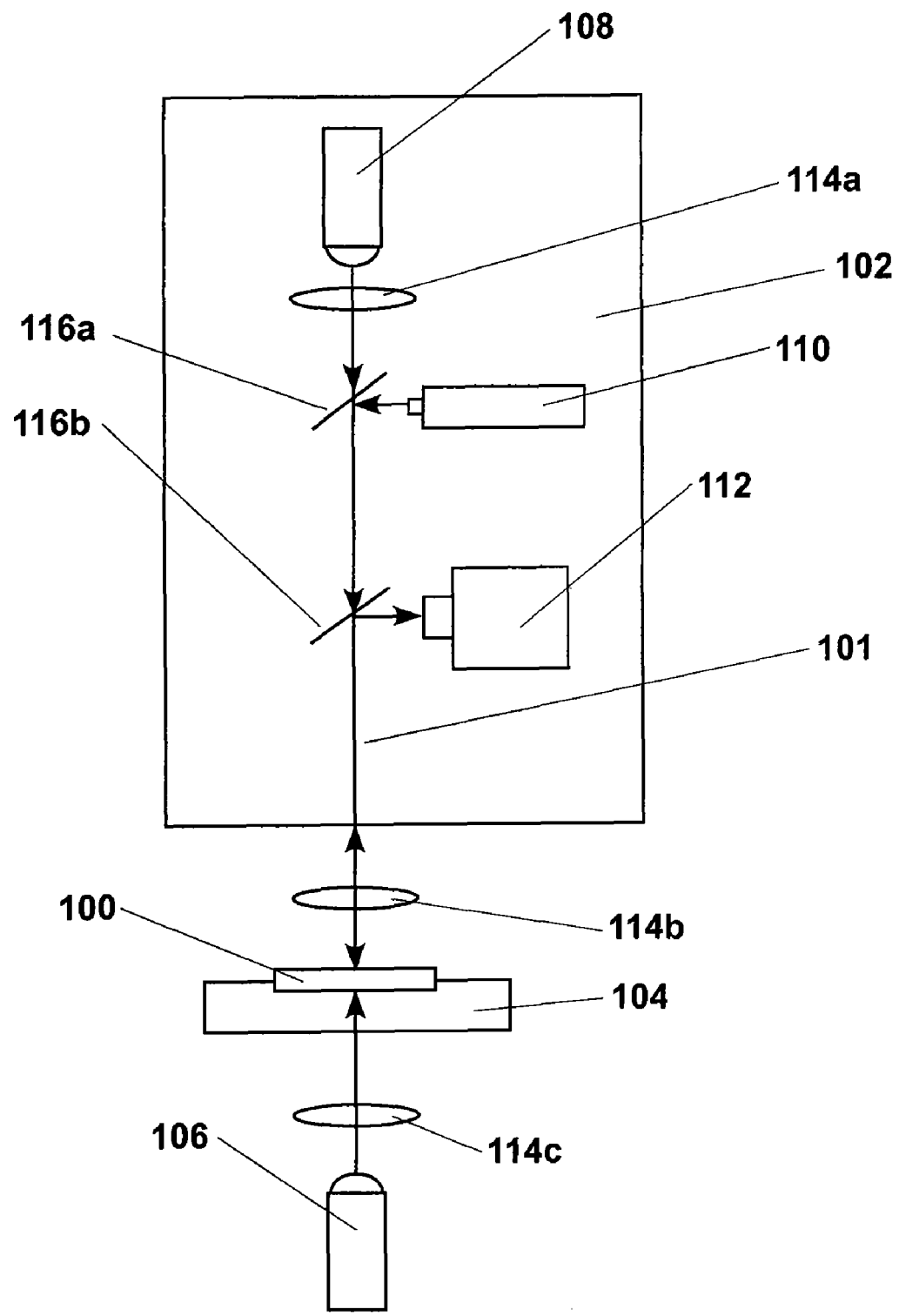
FIG. 1 depicts an embodiment of the disclosed apparatus for locating and eliminating defects in accordance with the present disclosure.

FIG. 1 shows an example of the apparatus for locating and eliminating defects on a MEMS device 100, such as a quartz DRG. The apparatus consists of a laser micromachining workstation 102, an XY stage with a transparent platform 104 under the device 100 to hold and position the MEMS device 100. The MEMS device 100 can be illuminated from one side, in this example the underside, by a backlight illumination source 106. The laser micromachining workstation 102 can consist of an illumination source 108 positioned to light the device 100 from the side opposite the side illuminated by the backlight illumination source 106. The workstation 102 can also include a laser 110 for ablating portions of the device 100 and an imaging system 112 for viewing the MEMS device 100 under magnification. The workstation 102 may also include partially reflective mirrors 116a and 116b to allow the laser 110 and the imaging system 112 to access the device 100 without interfering with the path 101 of light from the two illumination sources 106 and 108. Lenses 114a-c can be used to focus the light 101 onto the device 100 to aid in imaging and ablation.

Figure 2:
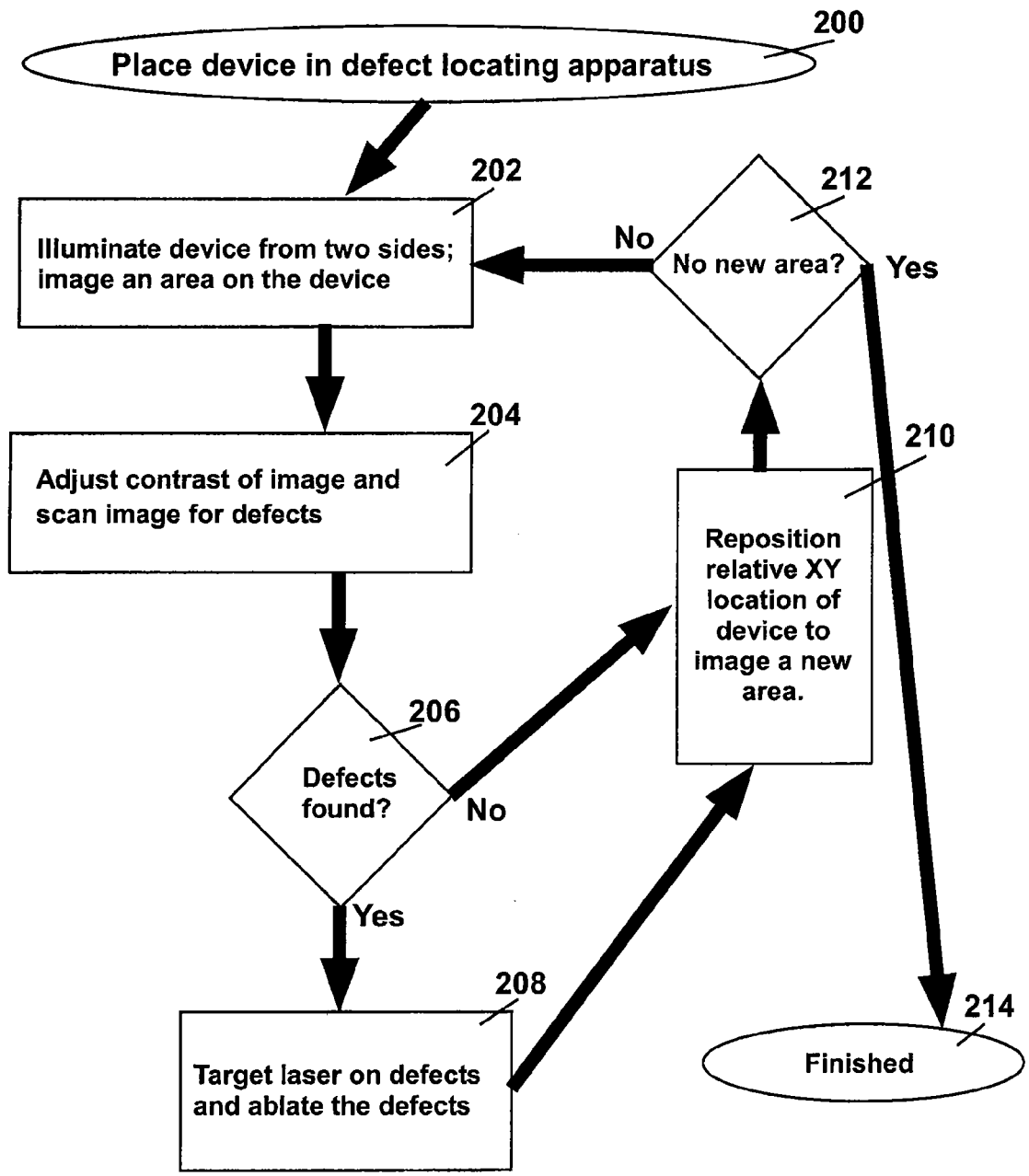
FIG. 2 shows a flowchart for an embodiment of a method for locating and eliminating manufacturing defects in accordance with the present disclosure.
Figure 6:
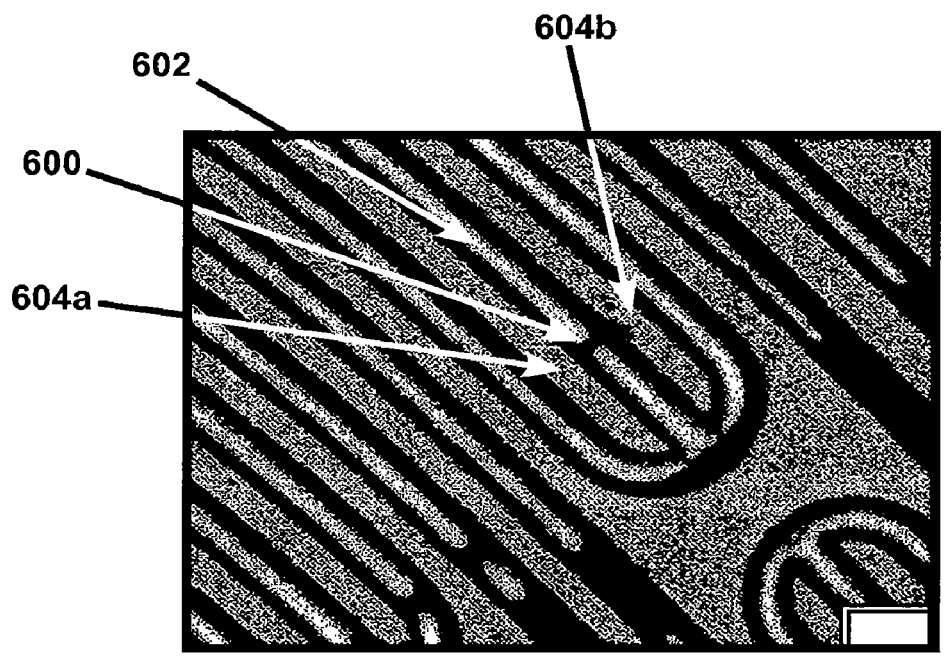
FIG. 6 depicts a DRG with a located defect bridging defect prior to laser ablation in accordance with the present disclosure.

FIG. 2 shows a flowchart of an example method for detecting and removing defects on a MEMS device. The apparatus shown in FIG. 1 can be utilized to carry out the method, but other equivalent systems can be used as well. First, the device 100 is held in place in a way that allows access to both sides of the device, which is generally a flat die or wafer structure, at the same time. For example, the device 100 can be affixed in step 200 to the transparent platform 104. The device 100 is then illuminated in step 202 on both the top and bottom surfaces by illumination sources 106 and 108 that the device material is semi-transparent to. For example, if the device is constructed from quartz, visible light can be used. If the device is silicon, then infrared light can be used. An imaging system 112, such as a camera, is used to view the device in step 202 from one of the sides, for example the top-side. If infrared light is used for illumination, then the imaging system 112 would have to be able to translate infrared images into a visible image. The imaging system 112 can magnify the image as needed to make any defects easier to detect. An area of the device 100 is scanned for defects in etched regions of the device 100. The image contrast is adjusted in step 204 to accentuate the point defects, such as unwanted bridges between device structures. The defects appear dark, since they tend to scatter and block the backside illumination from illumination source 106. An example is shown in FIG. 6. Once a defect is detected in step 206, an excimer laser 110 can be used to ablate the defect from the device in step 208. For example, a 193 nm ultraviolet excimer laser can be used to ablate defects in quartz devices. The imaging system 112 and the laser 110 can be connected as to allow aiming of the laser through the imaging device. The transparent platform 204 is adjusted in step 210 to allow viewing of different areas of the device. This process is then repeated in step 212 until in step 214 all discovered defects are removed.

Figure 3:
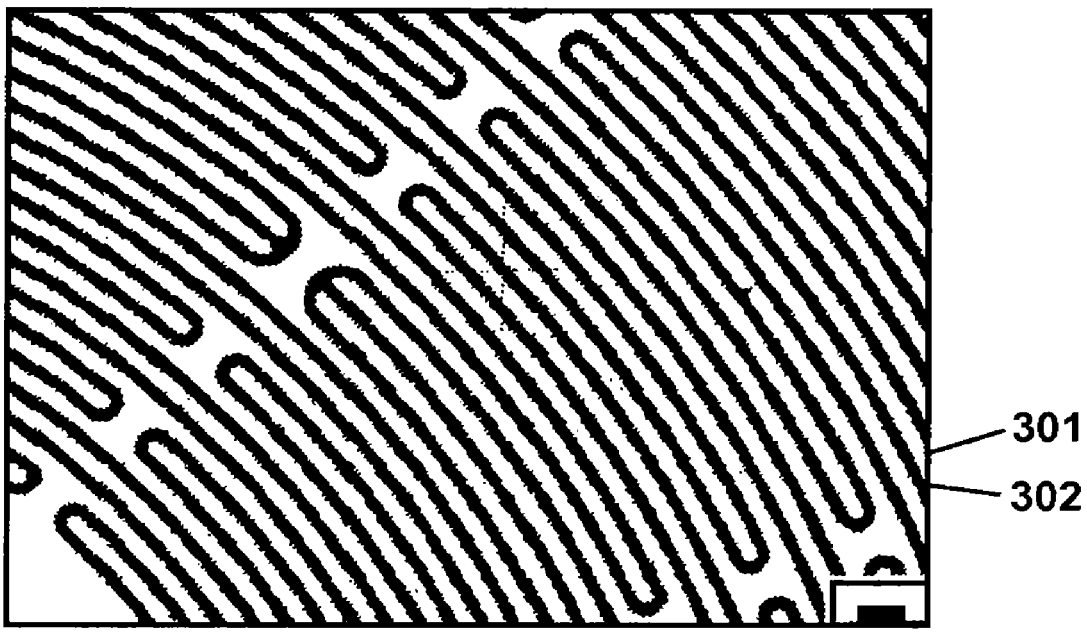
FIG. 3 depicts a DRG imaged from the top-side with top-side illumination of the DRG in accordance with the present disclosure.

FIG. 3 depicts an example of a DRG device imaged from the top with top-side illumination only. Because the device is partially reflective to the visible light in the case of quartz devices, and IR light in the case of silicon devices, the material portions 301 of the device appear white while the etched spaces 302 between the material portions 301 appear black.

Figure 4:
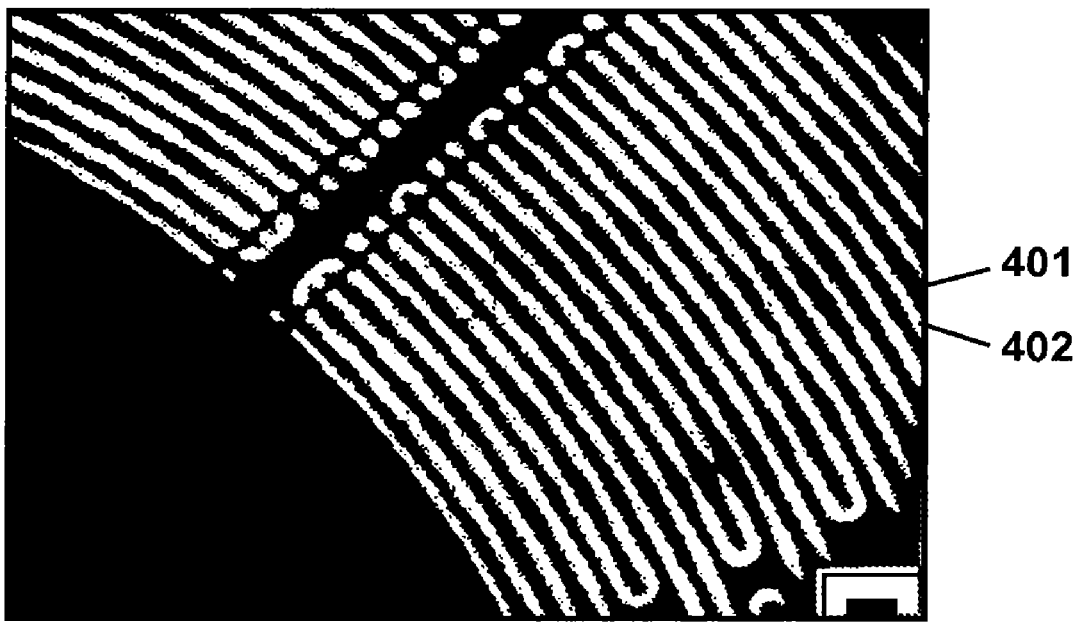
FIG. 4 depicts a DRG imaged from the top-side with bottom-side illumination of the DRG in accordance with the present disclosure.

FIG. 4 depicts an example of a DRG device imaged from the top with bottom-side or back side illumination only. Because the device is partially opaque, the material portions 401 appear black or dark and the etched spaces 402 between the material portions 401 appear white.

Figure 5:
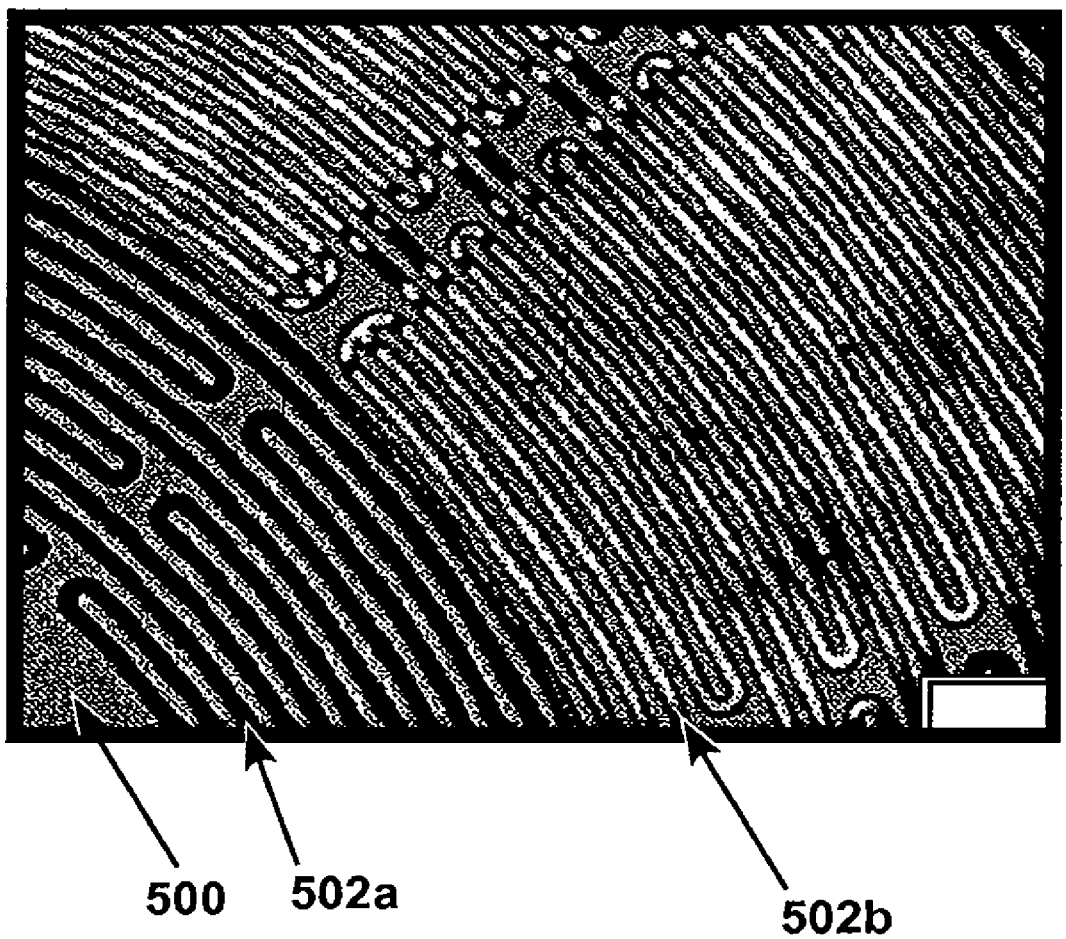
FIG. 5 depicts a DRG imaged from the top-side with a combination of top-side and bottom-side illumination of the DRG in accordance with the present disclosure.

FIG. 5 depicts an example of a DRG device imaged from the top with both bottom-side and top-side illumination. The material portions 500 appear grey, while the etched spaces 502a and 502b appear either black 502a or white 502b, depending on the geographic structure and positioning of the device and the illumination sources.

FIG. 6 depicts an example of an image of a DRG device with a defect 600 imaged with a combination of top-side and bottom-side illumination. The defect 600 is a bridging or masking defect causing a bridge of material to extend from one portion 604a of the DRG device to another portion 604b. This causes the portions 604a and 604b to be pinned together preventing them from resonating properly. In addition, when the DRG is metallized, the bridge would cause a short which would alter the electrical properties of the DRG. The combination top side and bottom side illumination allows the defect 600 to be clearly seen as a dark patch on the etched space 602.

Figure 7:
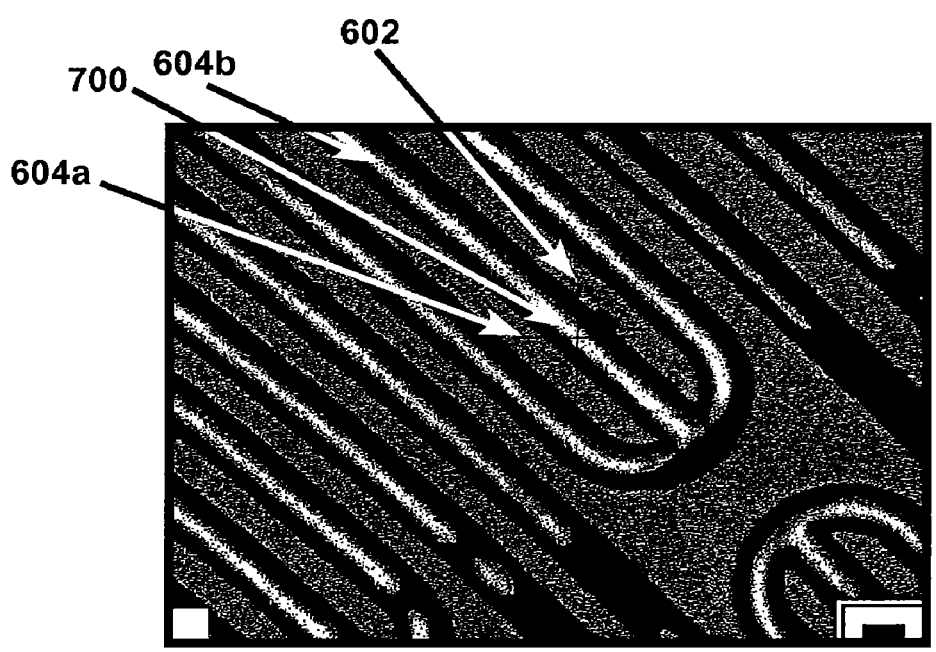
FIG. 7 depicts a DRG with a located defect bridging defect after laser ablation of the defect in accordance with the present disclosure.

FIG. 7 depicts an example of an image of the DRG device of FIG. 6 after ablation of the defect with the laser 110. FIG. 7 reference 700 shows the previous location of the defect, which in FIG. 7 matches the tint of the rest of the etched space 602 which indicates that the defect is now removed. The surrounding DRG material 604*a* and 604*b* is unaffected by the ablation as the laser is focused to an area smaller than the width of the etched space 602.

Additionally, electrical and mechanical testing can be utilized to assist in the determination of defects, followed by the localization and eliminated of these defects, by this apparatus. The same techniques can be utilized to eliminate electrical shorting defects on base wafers used subsequently to assemble finished DRG's.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the steps of . . . "

What is claimed is:

1. An apparatus for locating and eliminating defects on a substrate wafer, comprising:
   an adjustable transparent base for holding a bottom surface of the substrate wafer;
   a first illumination source for illuminating a top surface of the substrate wafer;
   a second illumination source for illuminating the bottom surface of the substrate wafer;
   an imaging system aligned to form an image of a portion of the top surface of the substrate wafer, the imaging system adapted to find defects in the image; and
   a laser aligned to the top surface of the substrate wafer for ablating the defects.

2. The apparatus of claim 1 wherein the imaging system comprises at least one adjustment for adjusting a contrast of the image.

3. The apparatus of claim 1 wherein:
   the substrate wafer comprises quartz;
   the first illumination source comprises visible light; and
   the second illumination source comprises visible light.

4. The apparatus of claim 3 wherein the laser comprises a 193 nm wavelength ultraviolet excimer laser capable of ablating quartz.

5. The apparatus of claim 1 wherein:
   the substrate wafer comprises silicon;
   the first illumination source comprises infrared illumination; and
   the second illumination source comprises infrared illumination.

6. The apparatus of claim 1 wherein:
   the substrate wafer is at least partially reflective of the first illumination source; and
   the substrate wafer is at least partially opaque to the second illumination source.

7. The apparatus of claim 1 wherein the substrate wafer comprises a quartz disc resonator for a disk resonator gyroscope (DRGs).

8. The apparatus of claim 1 further comprising:
   a first lens between the first illumination source and the substrate wafer, the first lens adjustable to adjust a contrast of the image; and
   a second lens between the second illumination source and the substrate wafer, the second lens adjustable to adjust the contrast of the image.

9. The apparatus of claim 1 further comprising:
   a first partially reflective mirror between the first illumination source and the substrate wafer for coupling an output of the laser to the substrate wafer; and
   a second partially reflective mirror in the first path for coupling the imaging system for imaging of the top surface of the substrate wafer.

* * * * *